United States Patent
Chung et al.

(10) Patent No.: US 10,393,693 B2
(45) Date of Patent: Aug. 27, 2019

(54) FLAT PLATE-TYPE OXYGEN SENSOR ELEMENT

(71) Applicant: AMOTECH CO., LTD., Incheon (KR)

(72) Inventors: Yeon-Soo Chung, Incheon (KR); Kil Jin Park, Incheon (KR); Sung-Jin Hong, Gyeonggi-do (KR); Soo-Min Oh, Seoul (KR); Eun-Ji Kim, Incheon (KR)

(73) Assignee: AMOTECH CO., LTD., Incheon (KR)

( * ) Notice: Subject to any disclaimer, the term of this patent is extended or adjusted under 35 U.S.C. 154(b) by 367 days.

(21) Appl. No.: 15/519,777

(22) PCT Filed: Oct. 15, 2015

(86) PCT No.: PCT/KR2015/010892
§ 371 (c)(1),
(2) Date: Apr. 17, 2017

(87) PCT Pub. No.: WO2016/060493
PCT Pub. Date: Apr. 21, 2016

(65) Prior Publication Data
US 2017/0241941 A1  Aug. 24, 2017

(30) Foreign Application Priority Data

Oct. 17, 2014  (KR) .................. 10-2014-0140764
Oct. 17, 2014  (KR) .................. 10-2014-0140765

(51) Int. Cl.
*G01N 27/407* (2006.01)
*F01N 11/00* (2006.01)
*G01N 27/406* (2006.01)

(52) U.S. Cl.
CPC ......... *G01N 27/4071* (2013.01); *F01N 11/00* (2013.01); *G01N 27/4067* (2013.01);
(Continued)

(58) Field of Classification Search
CPC .............................. G01N 27/406–41
See application file for complete search history.

(56) References Cited

U.S. PATENT DOCUMENTS 4,824,548 A * 4/1989 Iino ................ G01N 27/4065
                                                                    204/406
2002/0108855 A1  8/2002 Wang et al.

FOREIGN PATENT DOCUMENTS

JP  2002-310988 A  10/2002
JP  2004-117099 A   4/2004
(Continued)

OTHER PUBLICATIONS

International Search Authority/KR, International Search Report dated Feb. 19, 2016 in International Patent Application No. PCT/KR2015/010892 (with English translation), 4 pages.

*Primary Examiner* — J. Christopher Ball
(74) *Attorney, Agent, or Firm* — Masuvalley & Partners

(57) ABSTRACT

Provided is a flat plate-type oxygen sensor element. The flat plate-type oxygen sensor element according to an exemplary embodiment of the present invention includes: a first electrolyte layer having a sensing electrode exposed to a target gas; a second electrolyte layer on which a reference electrode is disposed; and a heating unit having a heating resistor surrounded by an insulating layer and disposed between the sensing electrode and the reference electrode, wherein the heating unit is disposed so that the heating resistor is located at a position ranging from 40 to 60% of a total height from an upper surface of the first electrolyte layer to a lower surface of the second electrolyte layer.

19 Claims, 7 Drawing Sheets

(52) U.S. Cl.
CPC ..... *G01N 27/4073* (2013.01); *G01N 27/4075* (2013.01); *F01N 2560/025* (2013.01); *F01N 2560/20* (2013.01); *Y02T 10/47* (2013.01)

(56) References Cited

FOREIGN PATENT DOCUMENTS

| | | |
|---|---|---|
| JP | 2004-163432 A | 6/2004 |
| JP | 2012-146449 A | 8/2012 |
| KR | 10-0148687 B1 | 8/1998 |
| KR | 10-2002-0060713 A | 7/2002 |

* cited by examiner

FLAT PLATE-TYPE OXYGEN SENSOR ELEMENT

RELATED APPLICATIONS

This application is a U.S. National Phase application under 35 U.S.C. § 371 of International Patent Application No. PCT/KR2015/010892 filed Oct. 15, 2015, which claims priority to Korean Patent Application No. 10-2014-0140764 filed Oct. 17, 2014 and Korean Patent Application No. 10-2014-0140765 filed Oct. 17, 2014, which are hereby expressly incorporated by reference in their entirety for all purposes.

TECHNICAL FIELD

The present invention relates to a flat plate-type oxygen sensor element.

BACKGROUND ART

An oxygen sensor is a device configured to measure oxygen partial pressure using a sensor used for a double oxygen sensor system and feedback the measured oxygen partial pressure to an engine control unit (ECU). Through this, a three way catalyst configured to eliminate nitrogen oxide (NOx), hydrocarbon (HC), and carbon monoxide (CO) included in an exhaust gas is used under an optimum condition.

A binary-type oxygen sensor which is being applied to most current vehicles uses oxygen included in the atmosphere being suctioned into a sensing unit through an inlet hole, which leads from a central portion of the oxygen sensor to the atmosphere, as reference oxygen to detect an oxygen concentration included in an exhaust gas.

In addition, when there is no atmosphere inlet hole, oxygen used for detecting an oxygen concentration in an exhaust gas is used by directly charging the exhaust gas into a reference electrode of an oxygen sensor element, and the oxygen is used as reference oxygen.

In this case, a planar-type oxygen sensor of the binary-type oxygen sensor uses zirconia, which is a typical oxygen ion conductor, as a medium for detecting an amount of exhausted oxygen.

In such a planar-type oxygen sensor, a sensing electrode is disposed on a detecting surface to be exposed to an exhaust gas, a reference electrode is disposed in a solid electrolyte layer to be located in a portion under the sensing electrode, and a heating unit configured to heat the solid electrolyte layer is disposed in a portion under the reference electrode.

Because of this, since the solid electrolyte layer is sequentially and upwardly heated by the heating unit, there is a problem in that a total response speed is slow.

In addition, since a heating unit made of a different material from the other components is biased toward and disposed at a lower side in an entire structure thereof, differences in expansion and contraction rates occur due to a difference in a material thereof when expansion occurs by sintering or heating, and thus there is a problem in that cracking or bending occurs.

Meanwhile, an electrical connection structure among a heating unit, a reference electrode, and a terminal is configured such that a via hole of the heating unit is formed vertically downward and a via hole of the reference electrode is formed vertically upward so as to be connected to the terminal.

However, when a heating unit is disposed between a reference electrode and a sensing electrode and via holes are formed in a conventional manner, there is a structural problem in that the via holes configured to connect the reference electrode and a terminal have to be pass through the heating unit to be installed.

Accordingly, a new method for solving these problems is required.

DISCLOSURE

Technical Problem

The present invention is directed to providing a flat plate-type oxygen sensor element capable of achieving structural stability and an improved response speed by disposing a heating unit between a sensing electrode and a reference electrode.

In addition, the present invention is directed to providing a flat plate-type oxygen sensor element in which a plurality of via holes configured to be connected to corresponding terminals do not overlap each other and are connectable to the terminals through a simple structure when a heating unit is disposed between a sensing electrode and a reference electrode.

Technical Solution

One aspect of the present invention provides a flat plate-type oxygen sensor element including: a first electrolyte layer including a sensing electrode exposed to a target gas; a second electrolyte layer which is disposed in a portion under the first electrolyte layer and on which a reference electrode is disposed on an upper surface of the second electrolyte layer; and a heating unit in whch a heating resistor surrounded by an insulating layer and which is disposed between the sensing electrode and the reference electrode, wherein the heating unit is disposed so that the heating resistor is located at a position ranging from 40 to 60% of a total height from an upper surface of the first electrolyte layer to a lower surface of the second electrolyte layer.

The reference electrode may be disposed to be in contact with a lower surface of the heating unit.

A third electrolyte layer having a predetermined height may be disposed between the heating unit and the second electrolyte layer.

The heating unit may include an open portion so that oxygen ions transmitted from the sensing electrode pass through.

The heating resistor may be disposed to be located at a central portion of the total height from the upper surface of the first electrolyte layer to the lower surface of the second electrolyte layer, and an upper portion and a lower portion thereof may be disposed symmetrically with respect to the heating unit.

The first electrolyte layer and the second electrolyte layer may be provided to have the same height, and the heating resistor of the heating unit may be disposed to be located at the central portion of the total height from the upper surface of the first electrolyte layer to the lower surface of the second electrolyte layer.

The first electrolyte layer and the second electrolyte layer may be made of the same material.

A sum of a height of the second electrolyte layer and the height of the third electrolyte layer may be the same as a height of the first electrolyte layer, and the heating resistor of the heating unit may be disposed to be located at a central portion of the total height from the upper surface of the first electrolyte layer to the lower surface of the second electrolyte layer.

The first electrolyte layer, the second electrolyte layer, and the third electrolyte layer may be made of the same material.

A buffer layer having the same height as the heating unit may be disposed between the first electrolyte layer and the second electrolyte layer to surround the heating unit.

Another aspect of the present invention provides a flat plate-type oxygen sensor element including: a first electrolyte layer on which a sensing electrode and an upper terminal are disposed on one surface of the first electrolyte layer; a second electrolyte layer on which a reference electrode and a first lower terminal are disposed on opposite surfaces of the second electrolyte layer; and a heating unit in which a heating resistor having a first connection portion and a second connection portion is surrounded by an insulating layer and which is disposed between the first electrolyte layer and the second electrolyte layer, wherein either the first connection portion or the second connection portion of the heating resistor is disposed directly under the sensing electrode and is connected to the first lower terminal through a second via hole formed to pass through the second electrolyte layer from the heating resistor, and the other connection portion is connected to an upper terminal through a first via hole formed to pass through the first electrolyte layer from the heating resistor.

A second lower terminal disposed beside the first lower terminal may be formed on a lower surface of the second electrolyte layer, the second lower terminal may be disposed in a portion directly under the upper terminal, and the first lower terminal may be disposed in a portion directly under the sensing electrode.

The second lower terminal may be connected to the reference electrode through a third via hole formed to pass through the second electrolyte layer.

The insulating layer may include a first insulating layer disposed in a portion over the heating resistor and a second insulating layer disposed in a portion under the heating resistor, the first via hole may be formed to pass through both the first insulating layer and the first electrolyte layer from the heating resistor, and the second via hole may be formed to pass through both the second insulating layer and the second electrolyte layer from the heating resistor.

The reference electrode may be disposed to be in contact with a lower portion of the second insulating layer, a third insulating layer may be disposed in a portion under the reference electrode, and each of the second via hole and the third via hole are formed to pass through the third insulating layer from the heating resistor and the reference electrode.

The reference electrode may be surrounded by a pair of insulating layers disposed on upper and lower surfaces of the reference electrode, a third electrolyte layer having a predetermined height may be disposed between the reference electrode and the heating unit, the second via hole may be formed to pass through both the third electrolyte layer and the second electrolyte layer from the heating resistor, and the third via hole may be formed to pass through both the insulating layer and the second electrolyte layer disposed in the portion under the reference electrode from the reference electrode.

Advantageous Effects

According to the present invention, since a heating unit is disposed between a sensing electrode and a reference electrode, structural stability and an improved response speed can be achieved.

In addition, according to the present invention, a plurality of via holes configured to connected to corresponding terminals do not overlap each other and can be connected to the corresponding terminals through a simple structure.

MODES OF THE INVENTION

Figure 1:
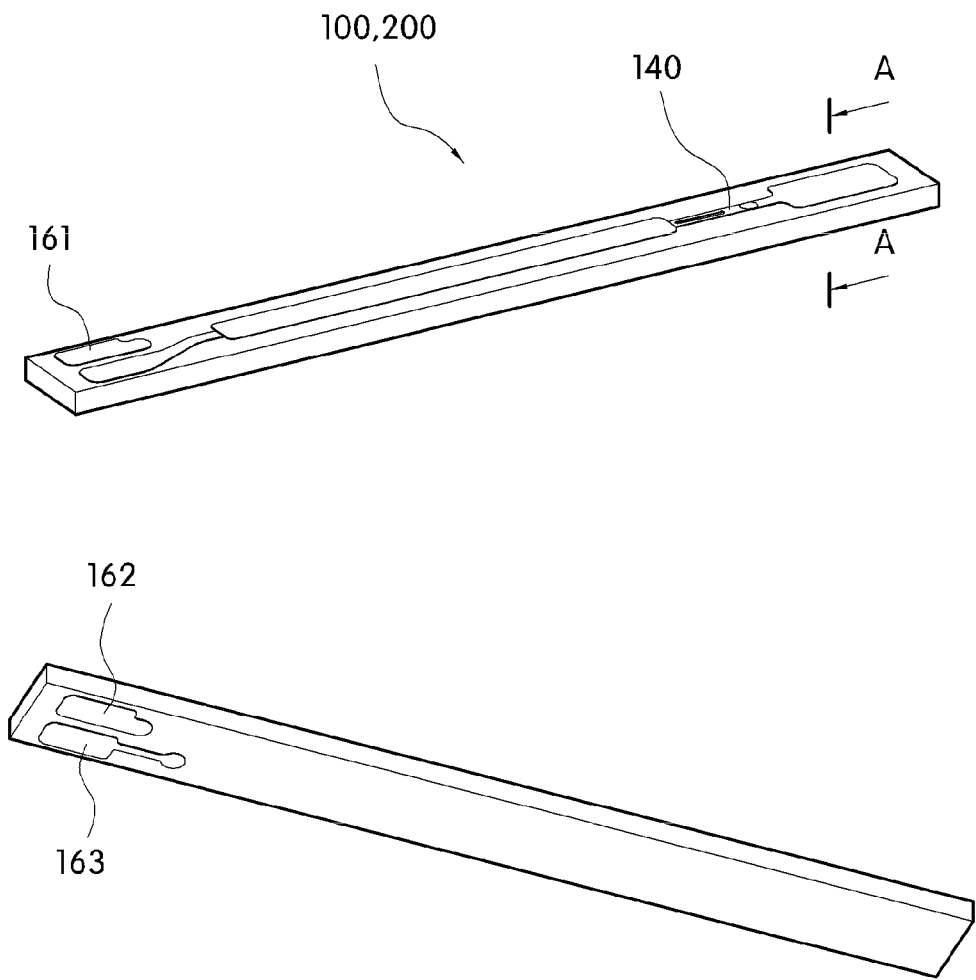
FIG. 1 is a perspective view illustrating an entire flat plate-type oxygen sensor element according to one embodiment of the present invention.

Hereinafter, embodiments of the present invention that may be easily performed by those skilled in the art will be described in detail with reference to the accompanying drawings. However, the embodiments of the present invention may be implemented in several different forms, and are not limited to the embodiments described herein. In addition, parts irrelevant to the description are omitted in the drawings in order to clearly explain embodiments of the present invention. Similar parts are denoted by similar reference numerals throughout this specification.

Referring to FIG. 1 to FIG. 7, flat plate-type oxygen sensor elements 100 and 200 according to one embodiment of the present invention includes a first electrolyte layer 110, a second electrolyte layer 120, and a heating unit 130.

The first electrolyte layer 110 is provided in a bar or film form having a predetermined height and in a flat plate-type having a predetermined area.

Here, the first electrolyte layer 110 is not particularly limited to a material as long as the material has oxygen ion conductivity. For example, the first electrolyte layer 110 may be made of yttrium stabilized zirconia (YSZ).

Such a first electrolyte layer 110 serves as a path through which oxygen ions transmitted from a sensing electrode 140 pass and move toward a reference electrode 150 or 250. That is, the first electrolyte layer 110 is disposed at an uppermost portion in an entire structure of an oxygen sensor element formed in a stacked type, and an upper surface thereof is a detecting surface exposed to a target gas.

In this case, the sensing electrode 140 exposed to the target gas and configured to detect an oxygen component from the target gas is disposed on the upper surface of the first electrolyte layer 110.

Such a sensing electrode 140 is made of gas-permeable porous platinum (Pt) and serves to deliver oxygen ions obtained from the target gas to the first electrolyte layer 110.

Meanwhile, a separate electrode protection layer (not shown) configured to protect the sensing electrode 140 from being contaminated by harmful components included in the target gas may be provided on the upper surface of the first electrolyte layer 110.

The second electrolyte layer 120 is disposed in a portion under the first electrolyte layer 110, and the reference electrode 150 or 250, in which the oxygen ions moved through the first electrolyte layer 110 are restored and collected, is disposed on an upper surface of the second electrolyte layer 120.

Here, the second electrolyte layer 120 is made of a material having oxygen ion conductivity, which is similar to the first electrolyte layer 110, so that oxygen ions move to surroundings of the reference electrode 150 or 250. It is preferable for such a second electrolyte layer 120 to be made of the same material as the first electrolyte layer 110 for structural stability when a coefficient of thermal expansion and the like due to sintering and heating is considered, and the second electrolyte layer 120 may be made of YSZ.

In addition, the reference electrode 150 or 250 disposed in a portion over the second electrolyte layer 120 serves to collect oxygen ions which pass through the first electrolyte layer 110 and is made of gas-permeable porous platinum (Pt), which is similar to the sensing electrode 140.

Accordingly, when negative and positive voltages are respectively applied to the sensing electrode 140 and the reference electrode 150 or 250, respectively, oxygen atoms in the target gas become oxygen ions after receiving electrons from the sensing electrode 140, then the oxygen ions are restored to oxygen atoms after passing through the first electrolyte layer 110, moving to the reference electrode 150 or 250, and releasing the electrons from the reference electrode 150 or 250, and then the oxygen atoms remain at the reference electrode 150 or 250.

Meanwhile, the reference electrode 150 or 250 may also be disposed in various patterns to control a pattern that the oxygen ions are collected in at the reference electrode 150 or 250.

Figure 2:
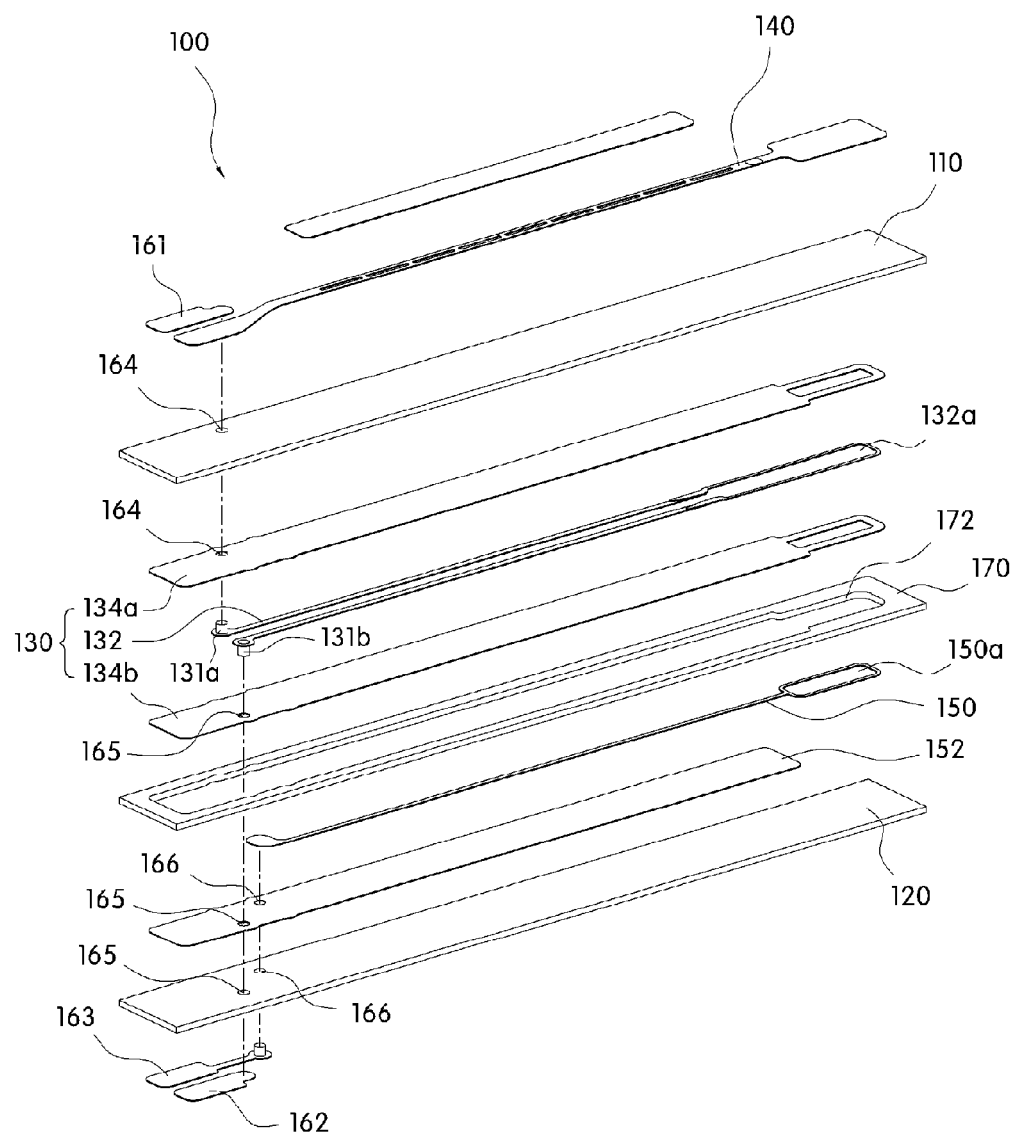
FIG. 2 is an exploded perspective view illustrating a flat plate-type oxygen sensor element according to a first embodiment of the present invention.

That is, as illustrated in FIG. 2, the reference electrode 150 disposed on the upper surface of the second electrolyte layer 120 may be disposed to be in direct contact with a lower surface of the heating unit 130, that is, more specifically, a lower surface of a second insulating layer 134B. In this case, a third insulating layer 152 is disposed between a lower surface of the reference electrode 150 and the second electrolyte layer 120, and the reference electrode 150 is surrounded by the second insulating layer 134B and the third insulating layer.

In this case, an entire upper surface of the reference electrode 150 is covered by the second insulating layer 134B, but the lower surface of the reference electrode 150 is surrounded by the third insulating layer 152 so that a part of the lower surface is exposed. In addition, an open portion 150A having a shape corresponding to an open portion 132A of the heating unit 130 is formed at one end portion of the reference electrode 150. Accordingly, oxygen ions moved from the sensing electrode 140 through the first electrolyte layer 110 pass through the open portion 132A of the heating unit 130, move downward through the open portion 150A of the reference electrode 150, and are then collected only at the lower surface of the reference electrode 150 to have a semicircular or semielliptical pattern.

Figure 5:
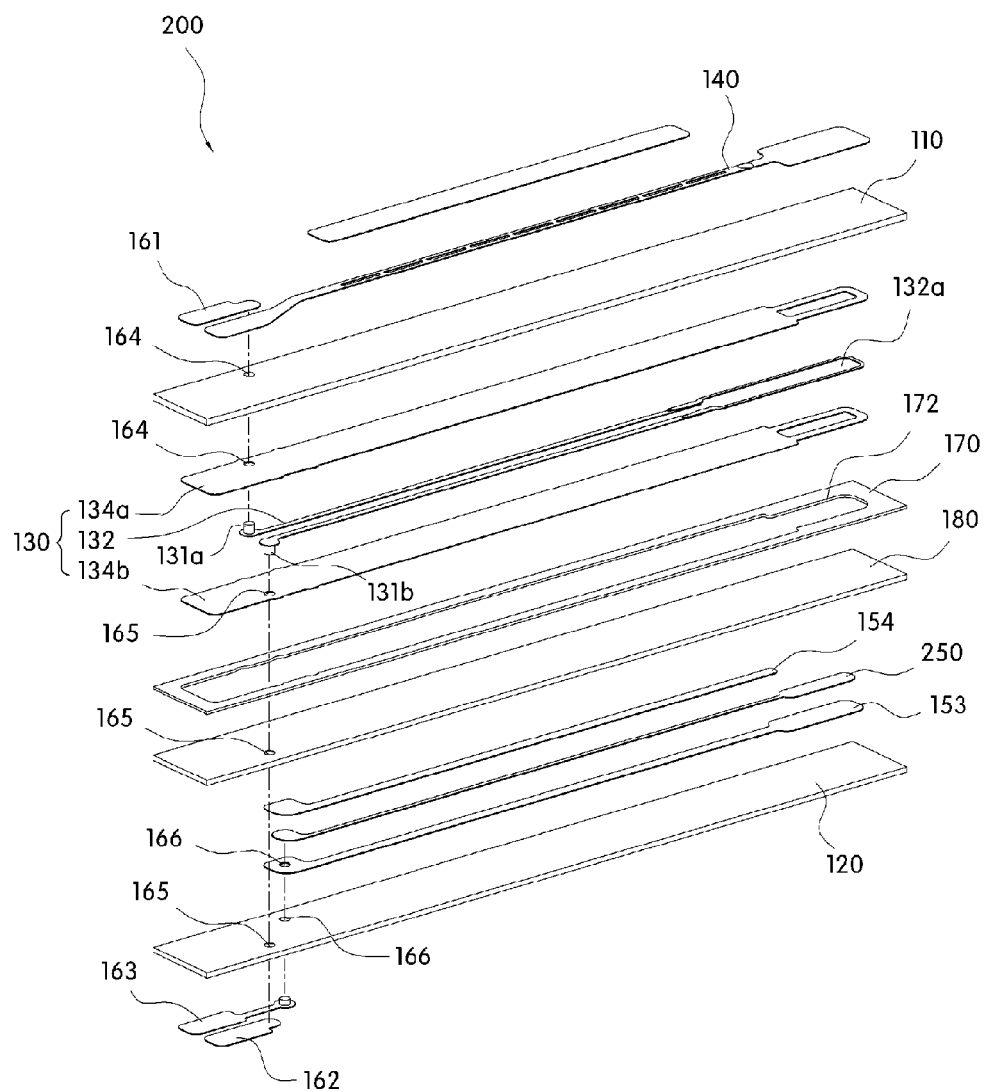
FIG. 5 is an exploded perspective view illustrating a flat plate-type oxygen sensor element according to a second embodiment of the present invention.

Alternatively, as illustrated in FIG. 5, the reference electrode 250 may also be disposed to be downwardly spaced a predetermined distance from the heating unit 130. To this end, a separate third electrolyte layer 180 having a predetermined height is disposed between the second electrolyte layer 120 and the heating unit 130, and the reference electrode 250 is disposed between the third electrolyte layer 180 and the second electrolyte layer 120.

Here, the third electrolyte layer 180 is also made of a material having oxygen ion conductivity so that oxygen ions may move to surroundings of the reference electrode 250, which is similar to the first electrolyte layer 110. It is preferable for such a third electrolyte layer 180 to be made of the same material as the first electrolyte layer 110 for structural stability when a coefficient of thermal expansion and the like due to sintering and heating is considered, and the third electrolyte layer 180 may be made of YSZ.

In this case, a fourth insulating layer 154 is disposed on an upper surface of the reference electrode 250, the third insulating layer 152 is disposed on a lower surface of the reference electrode 250 to cover a lead portion of the reference electrode 250, and a portion corresponding to the open portion 132A of the heating unit 130 is not covered by the insulating layer so as to be exposed.

Accordingly, oxygen ions moved from the sensing electrode 140 through the first electrolyte layer 110 pass through the open portion 132A of the heating unit 130 and the third electrolyte layer 180, and are then collected in a circular or elliptical pattern around the reference electrode 150 or 250.

In the flat plate-type oxygen sensor elements 100 and 200 according to one embodiment of the present invention, an arrangement distance between the heating unit 130 and the reference electrode 150 or 250 may be changed to control a pattern that oxygen ions are collected in the reference electrode 150 or 250, and thus performance of the oxygen sensor element may also be adjusted.

The heating unit 130 heats an electrolyte layer having ion conductivity to raise a temperature thereof. Such a heating unit 130 is provided such that a heating resistor 132 is completely surrounded by a pair of insulating layers 134A and 134B to remove noise generated during a heating process. That is, the pair of insulating layer 134A and 134B are provided as the first insulating layer 134A disposed in a portion over the heating resistor 132 and the second insulating layer 134B disposed in a portion under the heating resistor 132, and are disposed to completely surround the heating resistor 132.

Here, aluminum oxide ($Al_2O_3$) may be used as the insulating layers 134A and 134B, and a precious metal, tungsten, molybdenum, and the like may be used as the heating resistor 132. Pt, Au, Ag, Pd, Ir, Ru, Rh, and the like may be used as the precious metal, and only one thereof may be used as the precious metal, or two or more thereof may also be used together as the precious metal. In addition, it is preferable for the heating resistor to be made of the precious metal as a main component in consideration of heat resistance, oxidation resistance, and the like, and it is further preferable for the heating resistor to be made of Pt as a main component.

In this case, in the flat plate-type oxygen sensor elements 100 and 200 according to one embodiment of the present invention, the heating unit 130 is disposed to be located between the sensing electrode 140 and the reference electrode 150 or 250, unlike a conventional oxygen sensor element.

That is, the heating unit 130 is disposed to be located between the first electrolyte layer 110 in which the sensing electrode 140 is disposed on the upper surface thereof and the second electrolyte layer 120 in which the reference electrode 150 or 250 is disposed on the upper surface thereof, and more specifically, to be located at a position ranging from 40 to 60% of a total height H from the upper surface of the first electrolyte layer 110 to the lower surface of the second electrolyte layer 120.

Accordingly, since the first electrolyte layer 110 and the second electrolyte layer 120 through which oxygen ions move are disposed in portions over and under the heating unit 130, both the first electrolyte layer 110 and the second electrolyte layer 120 are directly heated by the heating unit 130. Because of this, since the electrolyte layers disposed in the portions over and under the heating unit 130 are simultaneously and directly heated, a time during which temperatures of the electrolyte layers are raised is decreased, and thus a total response speed may be increased unlike a conventional case in which electrolyte layers are sequentially upwardly heated by the heating unit 130 when the heating unit 130 is heated.

Here, the heating unit 130 disposed between the first electrolyte layer 110 and the second electrolyte layer 120 is provided to have the open portion 150A having a predetermined area so that oxygen ions pass from the sensing electrode 140 disposed in the portion of above the heating unit 130 to the reference electrode 150 disposed in the portion under the heating unit 130.

Meanwhile, a buffer layer 170 having the same height as the heating unit 130 may also be disposed between the first electrolyte layer 110 and the second electrolyte layer 120 to reduce a height deviation of the heating unit 130 when the heating unit 130 is disposed between the first electrolyte layer 110 and the second electrolyte layer 120.

In another embodiment in which the third electrolyte layer 180 is provided in a portion over the reference electrode 250, the buffer layer 170 is disposed between the first electrolyte layer 110 and the third electrolyte layer 180.

Such a buffer layer 170 is made of a material having oxygen ion conductivity, and a through hole 172 having a shape corresponding to the heating unit 130 is formed in the buffer layer 170. Accordingly, when the heating unit 130 is inserted into the through hole 172, a boundary of the heating unit 130 is surrounded by the buffer layer 170. Here, it is preferable for the buffer layer 170 to be made of the same material as the other electrolyte layers for structural stability when a coefficient of thermal expansion and the like due to sintering and heating is considered, and the buffer layer 170 may be made of YSZ.

Even though the buffer layer 170 is illustrated as being provided beside the heating unit 130 in the drawings, the present inventions is not limited thereto, and the second electrolyte layer 120 or the third electrolyte layer 180 may also be stacked to be in contact with a lower surface of the first electrolyte layer 110.

Meanwhile, in the flat plate-type oxygen sensor elements 100 and 200 according to one embodiment of the present invention, the heating unit 130 is disposed between the sensing electrode 140 and the reference electrode 150 or 250, and an upper portion and a lower portion thereof may be disposed symmetrically with respect to the heating unit 130.

That is, as illustrated in FIG. 2, when the reference electrode 150 is disposed directly in the portion under the heating unit 130, the heating resistor 132 of the heating unit 130 is disposed at a position corresponding to a center portion of the total height H from the upper surface of the first electrolyte layer 110 to the lower surface of the second electrolyte layer 120, and the upper portion and the lower portion thereof are disposed symmetrically with respect to the heating unit 130.

To this end, the first electrolyte layer 110 disposed in the portion on the heating unit 130 is provided to have a height H1 that is the same as a height H2 of the second electrolyte layer 120 disposed in the portion under the heating unit 130, and the heating resistor 132 of the heating unit 130 is located at a central portion of the total height H from the upper surface of the first electrolyte layer 110 to the lower surface of the second electrolyte layer 120.

In this case, the first electrolyte layer 110 and the second electrolyte layer 120 are made of the same material.

Accordingly, the heating unit 130 made of a material that is significantly different from the other components is disposed at a central portion of the entire structure, and the first electrolyte layer 110 and the second electrolyte layer 120 made of the same material are respectively disposed in the portions over and under the heating unit 130.

Because of this, since shrinkage rates of the electrolyte layers during a sintering process of manufacturing the oxygen sensor element are the same and expansion rates of the electrolyte layers due to heating of the heating unit 130 are the same, middle portions of the electrolyte layers in a lateral direction are prevented from being bent due to differences in the shrinkage rate and the expansion rate, and thus there is an advantage in that durability of the entire oxygen sensor element is improved.

In addition, as illustrated in FIG. 5, when the reference electrode 250 is disposed to be spaced a predetermined distance from the heating unit 130 by the third electrolyte layer 180 as a medium, a height H2', which is a sum of the height of the second electrolyte layer 120 disposed in the portion under the heating unit 130 and a height of the third electrolyte layer 180 in the portion under the heating unit, is the same as the height H1 of the first electrolyte layer 110 disposed in the portion over the heating unit 130.

Because of this, when the third electrolyte layer 180 is disposed, the heating resistor 132 of the heating unit 130 is also disposed to be located at a central portion of the total height H from the upper surface of the first electrolyte layer 110 to the lower surface of the second electrolyte layer 120.

Here, the heights of the second electrolyte layer 120 and the third electrolyte layer 180 may be half of the height of the electrolyte layer 110, but the heights are not limited thereto, and the heights of the second electrolyte layer 120 and the third electrolyte layer 180 may also be different from each other.

In this case, the first electrolyte layer 110, the second electrolyte layer 120, and the third electrolyte layer 180 are made of the same material having oxygen ion conductivity.

Accordingly, the heating unit 130 made of a material that is significantly different from the other components is located at a central portion of the entire structure, the first electrolyte layer 110 is disposed in the portion over the heating unit 130, and the second electrolyte layer 120 and the third electrolyte layer 180 having the same material as the first electrolyte layer 110 are disposed in the portion under the heating unit 130.

Because of this, since the shrinkage rates of the electrolyte layers during the sintering process for manufacturing the oxygen sensor element are the same and the expansion rates of the electrolyte layers due to the heating of the heating unit 130 are the same, the middle portions of the electrolyte layers in the lateral direction are prevented from being bent due to the differences in the shrinkage rate and the expansion rate, and thus there is an advantage in that durability of the entire oxygen sensor element is improved.

Meanwhile, via holes are disposed in alternate vertical directions so that the reference electrode 150 or 250 and the heating resistor 132 may be easily connected to the terminals when the heating unit 130 is disposed between the sensing electrode 140 and the reference electrode 150 or 250, which are similar to the flat plate-type oxygen sensor elements 100 and 200 according to one embodiment of the present invention.

In this case, an upper terminal 161 and the sensing electrode 140 are disposed on the upper surface of the first electrolyte layer 110, and two lower terminals 162 and 163 are disposed on the lower surface of the second electrolyte layer 120. Here, the two lower terminals 162 and 163 include the first lower terminal 162 connected to the a second connection portion 131B of the heating resistor 132 through a second via hole 165 and the second lower terminal 163 connected to the reference electrode 150 or 250 through a third via hole 166.

In addition, the first lower terminal 162 and the second lower terminal 163 are disposed side by side on the lower surface of the second electrolyte layer, the second lower terminal 163 is disposed in a portion directly under the upper terminal 161, and the first lower terminal 162 is disposed in a portion directly under a connection portion included in the sensing electrode 140.

In addition, the heating resistor 132 of the heating unit 130 includes a first connection portion 131A and the second connection portion 131B respectively electrically connected to the upper terminal 161 and the lower terminal 162 through the via holes.

In this case, a first via hole 164 configured to connect the first connection portion 131A of the heating resistor 132 and the upper terminal 161 is formed vertically upward to pass through the first electrolyte layer 110 from the first connection portion 131A, and the second via hole 165 configured to connect the second connection portion 131B of the heating resistor 132 disposed directly under a terminal of the sensing electrode 140 and the lower terminal 162 is formed vertically downward to pass through the second electrolyte layer 120.

That is, the first via hole 164 and the second via hole 165 are respectively formed upwardly and downwardly from the first connection portion 131A and the second connection portion 131B of the heating resistor 132 in alternate vertical directions to pass through the first electrolyte layer 110 and the second electrolyte layer 120 respectively disposed in the portions over and under the heating unit 130.

In this case, the first via hole 164 is formed to pass through both the first insulating layer 134A and the first electrolyte layer 110 disposed in the portion over the heating unit 130, and the second via hole 165 is formed to pass through both the second insulating layer 134B and the second electrolyte layer 120 disposed in the portion under the heating unit 130.

In addition, the third via hole 166 configured to connect a terminal of the reference electrode 150 or 250 and the second lower terminal 163 is formed to pass vertically downward through the second electrolyte layer 120 from the terminal of the reference electrode 150 or 250.

Here, since the second via hole 165 and the third via hole 166 respectively formed vertically downward from the second connection portion 131B and the terminal of the reference electrode 150 or 250 are disposed in alternate directions, the second via hole 165 and the third via hole 166 are not electrically connected.

Figure 3:
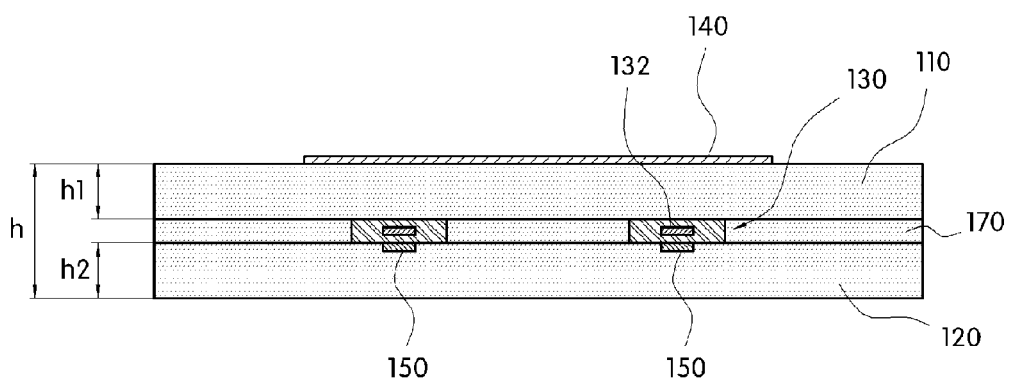
FIG. 3 is a cross-sectional view illustrating the flat plate-type oxygen sensor element according to the first embodiment, which is taken along line A-A in FIG. 1.
Figure 4:
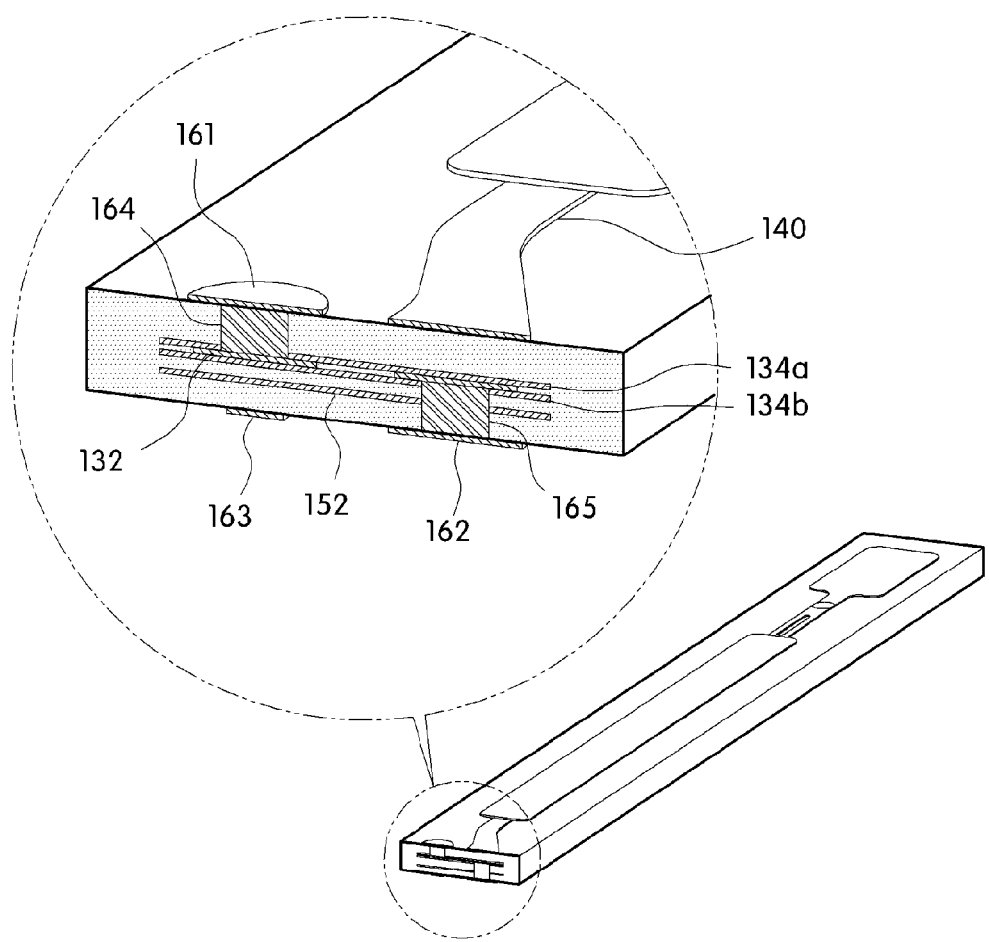
FIG. 4 is a partially cut-away view illustrating a relation of via holes in the flat plate-type oxygen sensor element according to the first embodiment of the present invention.

Meanwhile, as illustrated in FIGS. 2 and 3, when the reference electrode 150 is disposed directly under the second insulating layer 134B of the heating unit 130, both the second via hole 165 and the third via hole 166 are also formed to pass through the third insulating layer 152 disposed in a portion under the reference electrode 150.

Figure 6:
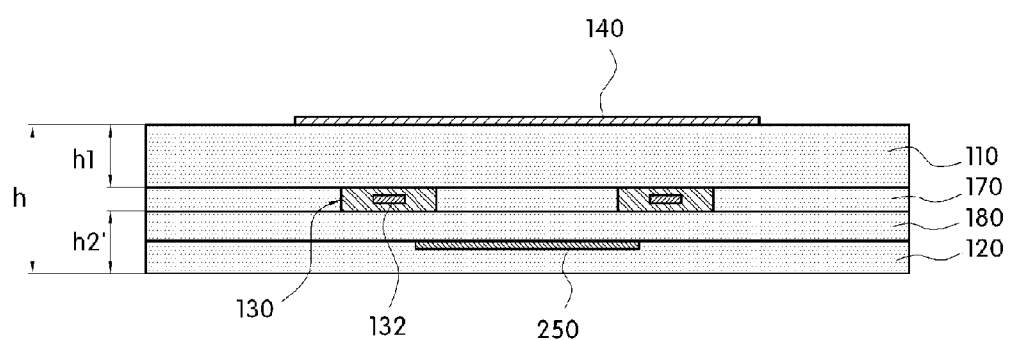
FIG. 6 is a cross-sectional view illustrating the flat plate-type oxygen sensor element according to the second embodiment, which is taken along line A-A in FIG. 1.
Figure 7:
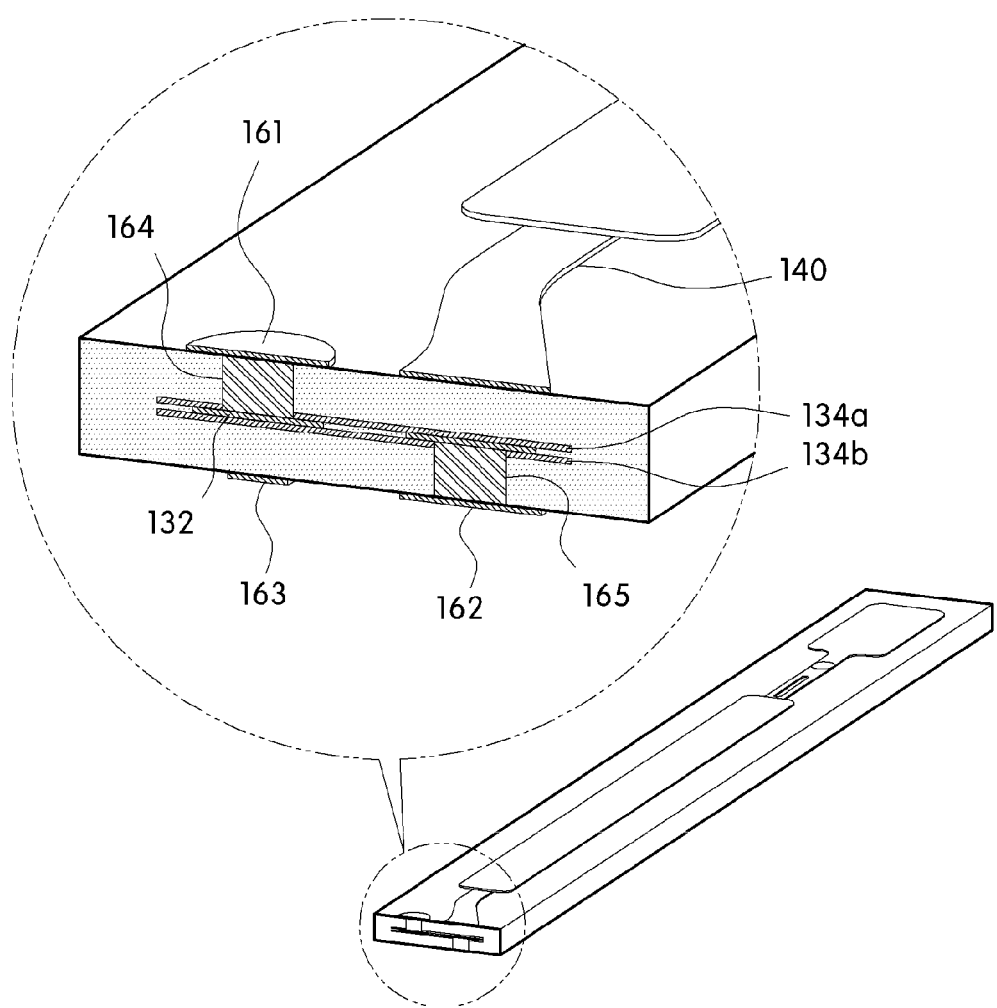
FIG. 7 is a partially cut-away view showing a relation of via holes in the flat plate-type oxygen sensor element according to the second embodiment.

In addition, as illustrated in FIGS. 5 and 6, when the third electrolyte layer 180 is disposed between the heating unit 130 and the second electrolyte layer 120 and the reference electrode 250 surrounded by the third insulating layer 152 and the fourth insulating layer 154 is disposed between the third electrolyte layer 180 and the second electrolyte layer 120, the second via hole 165 is formed to pass through both the third electrolyte layer 180 and the second electrolyte layer 120, and the third via hole 166 is formed to pass through both the third insulating layer 152 and the second electrolyte layer 120.

As described above, since the first via hole 164 is formed vertically upward and the second via hole 165 and the third via hole 166 are formed vertically downward on the basis of the heating unit 130, the third via hole 166 configured to connect the reference electrode 150 or 250 and the second lower terminal 163 can connect electrodes thereof without passing through the insulating layers 134A and 134B of the heating unit 130.

While embodiments of the present invention have been described above, the scope of the present invention is not limited thereto. Other embodiments may easily be made by those skilled in the art that understand the scope of the present invention by addition, modification, deletion, and the like of components, and these are also included in the range of the scope of the present invention.

The invention claimed is:

1. A flat plate-type oxygen sensor element comprising:
   a first electrolyte layer including a sensing electrode exposed to a target gas;
   a second electrolyte layer on which a reference electrode is disposed; and
   a heating unit having a heating resistor surrounded by an insulating layer and disposed between the sensing electrode and the reference electrode,
   wherein the heating unit is disposed so that the heating resistor is located at a position ranging from 40 to 60% of a total height from an upper surface of the first electrolyte layer to a lower surface of the second electrolyte layer.

2. The flat plate-type oxygen sensor element of claim 1, wherein the reference electrode is disposed to be in contact with the heating unit.

3. The flat plate-type oxygen sensor element of claim 2, wherein:
   the heating resistor is disposed to be located at a central portion of the total height from the upper surface of the first electrolyte layer to the lower surface of the second electrolyte layer; and
   an upper portion and a lower portion thereof are disposed symmetrically with respect to the heating unit.

4. The flat plate-type oxygen sensor element of claim 3, wherein:
   the first electrolyte layer and the second electrolyte layer are provided to have the same height; and
   the heating resistor of the heating unit is disposed to be positioned at the central portion of the total height from the upper surface of the first electrolyte layer to the lower surface of the second electrolyte layer.

5. The flat plate-type oxygen sensor element of claim 4, wherein the first electrolyte layer and the second electrolyte layer are made of the same material.

6. The flat plate-type oxygen sensor element of claim 1, wherein a third electrolyte layer having a predetermined height is disposed between the heating unit and the second electrolyte layer.

7. The flat plate-type oxygen sensor element of claim 6, wherein:
   a sum of a height of the second electrolyte layer and the height of the third electrolyte layer is the same as a height of the first electrolyte layer; and
   the heating resistor of the heating unit is disposed to be located at a central portion of the total height from the upper surface of the first electrolyte layer to the lower surface of the second electrolyte layer.

8. The flat plate-type oxygen sensor element of claim 7, wherein the first electrolyte layer, the second electrolyte layer, and the third electrolyte layer are made of the same material.

9. The flat plate-type oxygen sensor element of claim 6, wherein:
   the heating resistor is disposed to be located at a central portion of the total height from the upper surface of the first electrolyte layer to the lower surface of the second electrolyte layer; and
   an upper portion and a lower portion thereof are disposed symmetrically with respect to the heating unit.

10. The flat plate-type oxygen sensor element of claim 9, wherein:
    the first electrolyte layer and the second electrolyte layer are provided to have the same height; and
    the heating resistor of the heating unit is disposed to be positioned at the central portion of the total height from the upper surface of the first electrolyte layer to the lower surface of the second electrolyte layer.

11. The flat plate-type oxygen sensor element of claim 10, wherein the first electrolyte layer and the second electrolyte layer are made of the same material.

12. The flat plate-type oxygen sensor element of claim 1, wherein the heating unit includes an open portion so that oxygen ions transmitted from the sensing electrode pass therethrough.

13. The flat plate-type oxygen sensor element of claim 1, wherein a buffer layer having the same height as the heating unit is disposed between the first electrolyte layer and the second electrolyte layer to surround the heating unit.

14. A flat plate-type oxygen sensor element comprising:
    a first electrolyte layer on which a sensing electrode and an upper terminal are disposed on one surface of the first electrolyte layer;
    a second electrolyte layer on which a reference electrode and a first lower terminal are disposed on opposite surfaces of the second electrolyte layer; and
    a heating unit in which a heating resistor having a first connection portion and a second connection portion is surrounded by an insulating layer and which is disposed between the first electrolyte layer and the second electrolyte layer,
    wherein:
    either the first connection portion or the second connection portion of the heating resistor is disposed directly under sensing electrode and is connected to the first lower terminal through a second via hole formed to pass through the second electrolyte layer from the heating resistor; and
    the other connection portion is connected to an upper terminal through a first via hole formed to pass through the first electrolyte layer from the heating resistor.

15. The flat plate-type oxygen sensor element of claim 14, wherein:
    a second lower terminal disposed beside the first lower terminal is formed on one surface of the second electrolyte layer;
    the second lower terminal is disposed in a portion directly under the upper terminal; and
    the first lower terminal is disposed in a portion directly under the sensing electrode.

16. The flat plate-type oxygen sensor element of claim 15, wherein the second lower terminal is connected to the reference electrode through a third via hole formed to pass through the second electrolyte layer.

17. The flat plate-type oxygen sensor element of claim 16, wherein:
    the insulating layer includes a first insulating layer disposed in a portion over the heating resistor and a second insulating layer disposed in a portion under the heating resistor;
    the first via hole is formed to pass through both the first insulating layer and the first electrolyte layer from the heating resistor; and
    the second via hole is formed to pass through both the second insulating layer and the second electrolyte layer from the heating resistor.

18. The flat plate-type oxygen sensor element of claim 17, wherein:
    the reference electrode is disposed to be in contact with a portion of the second insulating layer;
    a third insulating layer is disposed in a portion under the reference electrode; and
    each of the second via hole and the third via hole is formed to pass through the third insulating layer from the heating resistor and the reference electrode.

19. The flat plate-type oxygen sensor element of claim 17, wherein:
    the reference electrode is surrounded by a pair of insulating layers disposed on upper and lower surfaces of the reference electrode;
    a third electrolyte layer having a predetermined height is disposed between the reference electrode and the heating unit;
    the second via hole is formed to pass through both the third electrolyte layer and the second electrolyte layer from the heating resistor; and
    the third via hole is formed to pass through both the insulating layer and the second electrolyte layer disposed in the portion under the reference electrode from the reference electrode.

* * * * *